United States Patent [19]

Brous

[11] Patent Number: 4,966,691
[45] Date of Patent: Oct. 30, 1990

[54] MEASUREMENT AND CONTROL OF ULTRAFILTRATION IN DIALYSIS

[76] Inventor: Donald W. Brous, P.O. Box 151, Manchester, N.H. 03105-0151

[21] Appl. No.: 351,220

[22] Filed: May 15, 1989

Related U.S. Application Data

[63] Continuation-in-part of Ser. No. 75,536, Jul. 20, 1987, abandoned.

[51] Int. Cl.⁵ .............................................. B01D 61/34
[52] U.S. Cl. ................................. 210/87; 210/321.65; 210/929
[58] Field of Search .................. 210/646, 87, 321.65, 210/321.71, 929

[56] References Cited

U.S. PATENT DOCUMENTS

| | | | |
|---|---|---|---|
| 3,946,731 | 3/1976 | Lichtenstein | 210/647 |
| 3,976,574 | 8/1976 | White | 210/929 |
| 4,021,341 | 5/1977 | Cosentino et al. | 210/87 |
| 4,060,485 | 11/1977 | Eaton | 210/87 |
| 4,148,314 | 4/1979 | Yin | 210/90 |
| 4,243,530 | 1/1981 | Lehnhoff et al. | 210/929 |
| 4,252,651 | 2/1981 | Soderstrom | 210/929 |
| 4,486,303 | 12/1984 | Brous | 210/321.65 |

*Primary Examiner*—W. Gary Jones
*Attorney, Agent, or Firm*—Munson H. Lane, Jr.

[57] ABSTRACT

Measuring and controlling dialysate flow to a dialyzer in hemodialysis by sensing the flow by an electric signal generating device and using this signal to indicate a differential between a preselected flow and an actual flow, and valving the flow according to this differential. The indication may be visual, and the signal can be used to automate the valving action.

5 Claims, 1 Drawing Sheet

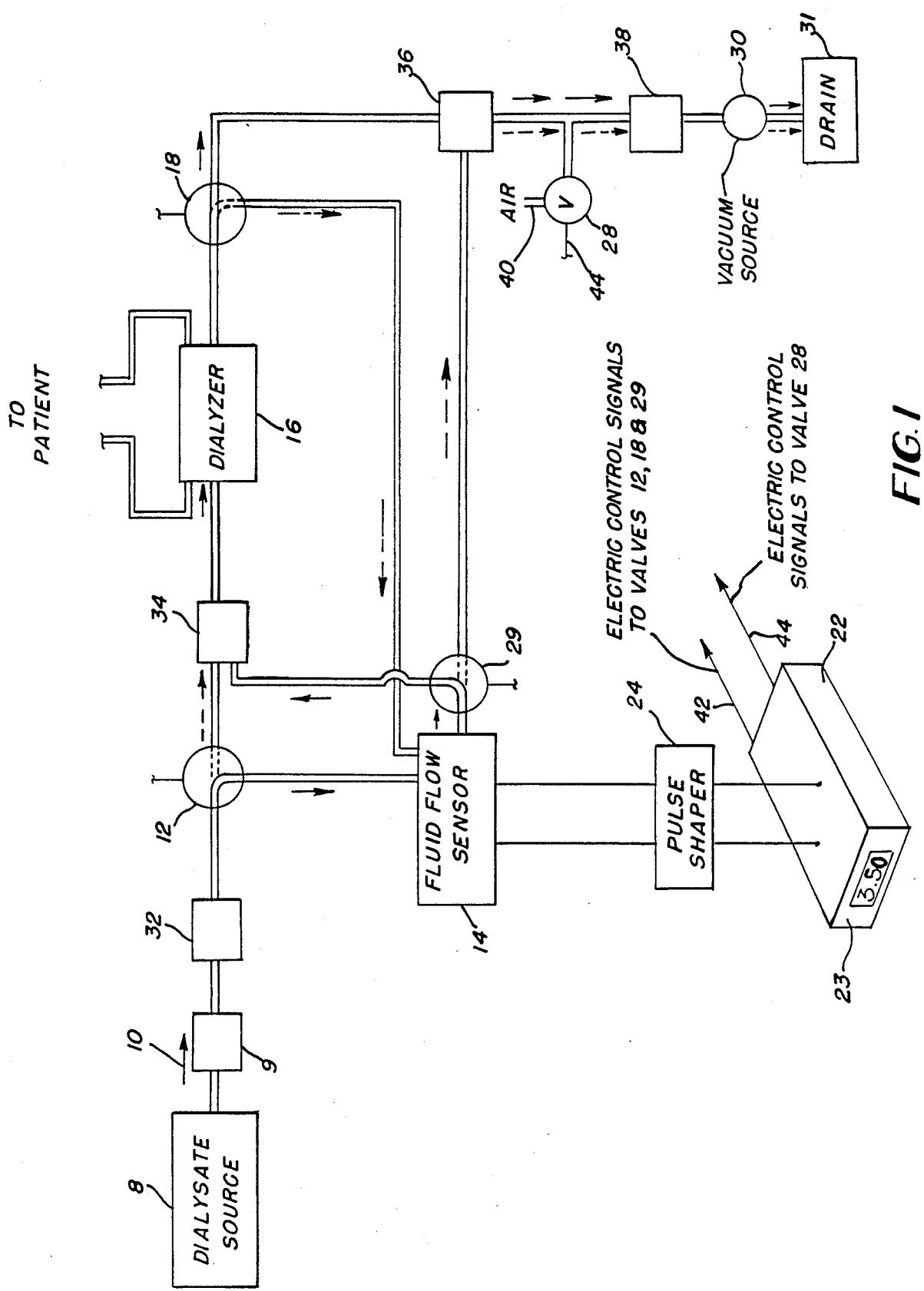

MEASUREMENT AND CONTROL OF ULTRAFILTRATION IN DIALYSIS

CROSS REFERENCE TO RELATED APPLICATION

This application is a continuation-in-part of pending application Ser. No. 7/075,536, filed July 20, 1987 by Donald W. Brous for Measurement and Control of Ultrafiltration in Dialysis now abandoned.

BACKGROUND OF THE INVENTION

1. Field of the Invention

This invention relates to measurement display and control of UFR (Ultrafiltration in Dialysis).

2. Description of the Prior Art

Special reference is made to U.S. Pat. No. 4,486,303, Dec. 4, 1984 as explaining some of the modes of measurement of ultrafiltration in hemodialysis, which is now a well-advanced procedure, depended upon by those who have diseased kidneys. The dialyzer is often referred to as an artificial kidney and saves many lives. However, in certain cases, there are hypotensive episodes due to too little or too much fluid removal. Patient tolerance, or lack of it, to fluid removal is an important factor, but often the dialyzer itself is a contributing factor. The hydraulic permeability is variable.

The current state-of-the-art (with most dialysate delivery systems) does not allow direct control of the rate of ultrafiltration but necessitates the control of transmembrane pressures to control ultrafiltration. The variability of hydraulic permeability can therefore result in variable and unpredictable ultrafiltration. In many dialysate delivery systems, only one pressure is measured on the dialysate side (dialyzer inlet or outlet pressure) and calculations of transmembrane pressure are based on this measured pressure rather than on the mean of the inlet and outlet pressures. As dialysate compartment pressure drops are small, this is normally not a source of large error. However, with some dialyzer designs, poor degassing of the dialysate results in high and variable dialysate compartment pressure drops. This is a consequence of "air locking" of dialysate flow passages. In such situations, ultrafiltration may be erratic and poorly controlled. In some dialyzer designs, the dialysate side pressure drop is a function of the transmembrane pressue because of membrane compliance with consequent changes in dialysate flow geometry. Erratic and unpredictable ultrafiltration may result with such dialyzers.

SUMMARY OF THE DISCLOSURE

The flow of dialysate into the dialyzer is measured by a "flowmeter" which generates electrical pulses or an electrical voltage proportional to the rate of dialysate flows. The electrical output of this flowmeter is a multiple of that of the fluid flow—for example, 500 cc/min. flow can produce 5,000 pulses/min or equivalent voltage. This electrical output is fed to a microprocessor based instrument.

By means of electrically operated solenoid valves, the dialysate flow into the flowmeter is then switched from the input to the dialyzer to the output of the dialyzer. Thus the flowmeter's electrical output then produces signals proportionate to the dialyzer input plus the "ultrafiltrate"—the fluid removed from the patient.

By design, the microprocessor displays zero when the input and output to the dialyzer are identical which would be the case when no negative pressure drop of the dialysate was generated, or when there was no positive pressure-drop in the blood compartment.

The microprocessor triggers the input and output dialyzer pulse signals by the same electrical circuit controlling the solenoid valves, which switch the dialysate path.

The microprocessor therefore displays the flow differential, which can be in any engineering units desired—fluid ounces or cc/minute; or grams or ounces of avoirdupois.

The cycling of these solenoid valves and the "samples" of counts can be adjusted to update the microprocessor as frequently as desired. Electronic "memory" will hold the differential reading between updating, so that only the actual, "real" ultrafiltration reading is displayed at all times.

The microprocessor also stores a running total of time minutes and hours of dialysis. It also accumulates the pounds or KG/hr. so the total fluid removal can be called up at any time during dialysis as well as total at the end of dialysis.

The microprocessor also has high-low electronic limits which can be set by the staff or patient as required. These limits, let us say when 3 lbs./hr. or 05 lbs./min. of fluid is to be removed, can be set to a few percent of variation from the desired rate and will control the negative pressure being exerted either by electrical valve or by pump motor speed or other method. In addition, any deviation from either high or low limits can be set to activate audible or visible alarms. The ultrafiltration is thereby controlled very accurately.

For retrofit of old dialysis machines, the instruments limits can control a valve to admit air between the dialysate output of the dialyzer and the negative pressure pump in the machine. This controlled introduction of air decreases the negative pressure being exerted, if it is out of limits. Conversely, closing the air valve will permit the negative pressure to increase if it is below the set limits.

BRIEF DESCRIPTION OF THE INVENTION

FIG. 1 is a flow chart of the invention showing the alternate flow paths for dialysate from the dialysate source to the dialyzer and for the dialysate plus ultrafiltrate from the dialyzer to drain, whereby the flow rate of dialysate entering the dialyzer and the flow rate of dialysate plus ultrafiltrate leaving the dialyzer are sampled alternately by the safe fluid flow sensor in succeeding intervals.

The flow path during one interval is shown by solid line arrows, while the alternate flow path during a second interval is shown by dotted line arrows.

PREFERRED EMBODIMENT OF THE INVENTION

This invention is disclosed in flow chart form only, because all the elements are obtainable commercially, and operation is by computer means, as will become clear to those conversant with the art.

The system disclosed in FIG. 1 includes a dialysate source 8, a proportioner 9, and a connector 32 connected in series by fluid conduits to a solenoid valve 12. The solenoid valve 12 in one position indicated by solid lines directs dialysate from the dialysate source to the fluid flow sensor 14, and in a second position indicated by dotted lines directs fluid flow to connector 34 and thence to the input side of the dialyzer 16. The output side of the dialyzer is connected by a conduit to a solenoid valve 18 which in one position, indicated by solid lines, directs the flow of dialysate plus ultrafiltrate to drain 31 through conduit connectors 36 and 38 and vacuum source 30, and in a second position indicated by dotted lines, directs the flow of dialysate plus ultrafiltrate to the fluid flow sensor 14.

The sensor 14 is a transducer producing electrical energy according to the fluid flow through it and it supplies an electrical signal output to a computer 22 through a pulse shaper 24. The sensor 14 is preferably a turbine which rotates at a speed in direct relation to the fluid flow through it and generates an electrical output which may be in the form of pulses, or voltage or current.

The pulse shaper 24 is an electronic amplifier (or similar device) to take the electrical output from the sensor 14 and to condition it to operate the computer/panel meter 22.

The computer/panel meter 22 is a microprocessor based electronic computer, in a panel instrument configuration. It accepts the electrical output from the sensor 14, as conditioned by the pulse shaper 24, and converts it to a digital quantity which it stores in its memory. Appropriate electrical connectors connect the electrical output of sensor 14 with the input side of pulse shaper 24 and connect the output side of the pulse shaper 24 with the input side of the computer/panel meter 22.

Fluid passing through the fluid flow sensor 14 is connected by a conduit to the solenoid valve 29. The valve 29 in one position shown by solid lines directs fluid from the fluid flow sensor 14 to the connector 34 and from thence to the dialyzer 16, and in a second position directs fluid from the fluid flow sensor 14 to the connector 36 and from thence to drain 31.

The solenoid valves 12, 18 and 29 are electrically connected to control line 42 from the computer/panel meter 22. Valve 12 is normally open for flow of dialysate to the sensor 14, or when power is applied through line 42, to close to sensor 14 and to open to the dialyzer 16 thus directing flow of dialysate directly to the dialyzer.

The solenoid valve 18 is normally open for flow from the dialyzer 16 to drain 31, or when power is applied through the line 42, it is closed to drain and open to the sensor 14 to direct dialysate and ultrafiltrate from the dialyzer to the sensor and then to drain.

The solenoid valve 29 is normally open for flow from the sensor 14 to the dialyzer 16, or when power is applied through line 42, it is closed to the dialyzer 16 and open to drain 31 thus directing dialysate and ultrafiltrate from the sensor 14 to drain 31.

The solenoid valve 28 is connected between ambient air and the fluid conduit connected between connectors 36 and 38 in the line going to vacuum source 30 and drain 31. It is normally closed to ambient air but upon opening the valve 28, air is admitted to the vacuum system which reduces the vacuum and hence reduces the rate of fluid removed from the patient to a predetermined level The valve 28 is electrically actuated to admit air to the vacuum system by electrical control signals received from the computer/panel meter 22 over line 44, when the meter reading exceeds a predetermined upper limit.

The computer/panel meter 22 samples the electrical output of the fluid flow sensor 14 at fixed intervals by electrically switching the solenoid valves 12, 18 and 29 so that fluid flow to the sensor alternates between the dialyzer input flow and the dialyzer output flow. It then subtracts the smaller flow reading from the higher flow.

If these two flows are identical (no ultrafiltration through the dialyzer), the meter reads zero.

If the output flow of the dialyzer 16 increases as the excess fluid is extracted from the blood flow (by pressure differentials), then the instrument displays this delta in engineering units—pounds per hr. or KG/hr., or in cc/minute or other values, if so desired.

The instrument 22 also has provision for setting hi-lo limits and if the digital display exceeds the limits, alarms can be turned on and/or a solenoid valve 28 opened to atmosphere to admit air into the vacuum (negative pressure/source) and thereby control the ultrafiltration rate to pre-determined levels The computer 22 is programmed to divert the flow coming out of the dialyzer for a predetermined interval from drain to the sensor 14 and thence to drain by means of the solenoid directional valves. The measured flow during this interval of output represents the actual ultrafiltration plus the basic input flow and the computer stores it and compares it with the previously measured input flow. The dialysate flow into the dialyzer by-passes the sensor 14 during the interval of sampling the dialyzer output.

Thus, the one sensor 14 alternately supplies the electrical information representing dialysate flow in and out of the dialyzer, into the computer, on a sampling basis, where it is digitized, stored and compared for each sampling interval. The differential representing ultrafiltrate flow is displayed digitally.

The computer incorporates adjustable hi-lo limits for control of alarms, indicators, valves, etc. Thus the fluid removed can be pre-programmed to maintain any weight loss.

The use of only one sensor to measure both input flow to the dialyzer and output flow from the dialyzer, obviates the necessity to match transducers exactly, and for correcting discrepancies between them.

There is no cessation of the flow of dialysate since only the direction of the dialysate in and out of the dialyzer and through the sensor, is changed. The flow of dialysate into the dialyzer remains constant, and is not changed by the "sampling" The switching of dialysate to the sensor is so fast that there is no discernible interruption.

The present invention as illustrated in FIG. 1 thus provides alternate dialysate flow paths whereby a single fluid flow rate meter (sensor 14) is enabled to alternately sample the flow rate of dialysate entering the dialyzer 16 during one interval and to sample the flow rate of dialysate plus ultrafiltrate leaving the dialyzer during a succeeding interval in continuing alternating sequence.

The solid arrows in FIG. 1 show the fluid flow path through the system when the valves 12, 18 and 29 are in one position, and the dotted line arrows show the fluid flow path through the system when the valves 12, 18 and 29 are in a second position.

In the first position of valves 12, 18 and 29, the dialysate flow, as shown by the solid line arrows, moves in a first input flow path from the dialysate source through valve 12, through the fluid flow sensor 14, through valve 29 to the dialyzer 16. The dialysate and any ultrafiltrate picked up in the dialyzer 16 moves in a first output flow path from the dialyzer 16 through the valve 18 to drain.

In the second position of valves 12, 18 and 29, the dialysate flow, as shown by the dotted line arrows, moves in a second input flow path from the dialysate source directly to the dialyzer 16 bypassing the fluid flow sensor 14. The dialysate and any ultrafiltrate picked up in the dialyzer 16, now moves in a second output flow path from the dialyzer 16 through the valve 18, through the fluid flow sensor 14, through the valve 29 to drain.

The vacuum source 30 is a vacuum pump or other means for applying a negative pressure to the fluid lines leading from the output side of the dialyzer 16. The fluid caused to flow by means of the vacuum source 30 is directed to the drain 31.

The method of the present invention for the measurement of ultrafiltrate in dialysis comprises the steps of:
   a. causing dialysate to flow through a dialyzer 16 wherein ultrafiltrate is removed from a patient and mixes with the dialysate,
   b. measuring during a first interval the flow rate of dialysate entering the dialyzer 16 with a flow rate sensor 14,
   c. measuring during a second interval the flow rate of dialysate and ultrafiltrate leaving the dialyzer 16 with the same sensor 14 which measures the flow rate of dialysate entering the dialyzer,
   d. comparing the flow rate of dialysate entering the dialyzer during the first interval with the flow rate of dialysate and ultrafiltrate leaving the dialyzer during the second interval to obtain the difference between the flow rates measured during steps (b) and (c), the difference corresponding to the flow rate of ultrafiltrate leaving the dialyzer.

The steps b and c recited above are repeated continuously in succeeding intervals of alternately measuring the flow rate of dialysate entering the dialyzer and the flow rate of dialysate and ultrafiltrate leaving the dialyzer for as long as the dialyzer is in use.

In the method of the present invention, it is preferred that the flow rate sensor 14 produce an electrical output signal which varies in direct proportion to the measured fluid flow rate The electric signal may be a pulse, voltage or current signal.

The present invention also includes a method for controlling ultrafiltrate flow in dialysis comprising steps a through c recited above with the following additional steps:
   d. computing the difference between the flow rate of the dialysate entering the dialyzer during the first interval and the flow rate of dialysate plus ultrafiltrate leaving the dialyzer during the second interval to produce an ultrafiltrate flow rate output signal,
   e. comparing the ultrafiltrate flow rate output signal with a predetermined ultrafiltrate flow rate norm, and
   f. varying the ultrafiltrate flow rate to keep the ultrafiltrate flow rate within predetermined levels relative to the aforesaid norm.

The step of varying the ultrafiltrate flow rate is preferably performed by varying negative pressure exerted on dialysate and ultrafiltrate leaving the dialyzer. While various means for varying the negative pressure may be employed within the scope of this invention, such as using a variable pressure vacuum pump 30, another method includes varying the negative pressure in the dialyzer output lines by controlled introduction of ambient pressure air into the line by means of a control valve 28 in order to maintain the flow rate of ultrafiltrate within predetermined high and low set point limits which are introduced into the computer/panel meter 22.

The display 23 on the computer/panel meter 22 is a digital display of the rate of flow of ultrafiltrate leaving the dialyzer 16 as computed by the computer 22.

The fluid connectors 32, 34, 36 and 38 are conventional quick connectors for connecting different parts of the present system together. The connector 32 is a Hansen male, the connector 34 is a Hansen female, the connector 36 is a Hansen female and the connector 38 is a Hansen male.

While in the foregoing there has been described and shown a preferred embodiment of the invention, various modifications and equivalents may be resorted to within the spirit and scope of the invention as claimed.

What is claimed is:

1. A system for measurement and control of ultrafiltration in dialysis comprising
   a dialyzer,
   a drain,
   a source of dialysate,
   means to cause dialysate to flow in the system,
   a sensor for measuring rate of flow,
   a first input flow path for conducting dialysate from said source to said sensor nd thence to said dialyzer,
   a second input flow path for conducting dialysate from said source directly to said dialyzer,
   a first output flow path for conducting dialysate and ultrafiltrate from said dialyzer to drain,
   a second output flow path for conducting dialysate and ultrafiltrate from said dialyzer to said sensor and thence to drain,
   a first control valve means in said first and second input flow paths for selectively directing flow of dialysate into said sensor or directly into said dialyzer,
   a second control valve means in said first and second output flow paths for selectively directing flow of dialysate and ultrafiltrate to drain or to said sensor,
   a third control valve means downstream of said sensor in said first input flow path and in said second output flow path for selectively directly flow from said sensor to said dialyzer or to said drain,
   said sensor generating an electric signal representing the fluid flow rate measured by said sensor,
   a computer having means for alternately controlling said first, second and third control valves means to direct fluid to flow first through said first input flow path into said dialyzer through said sensor, and out of said dialyzer to drain through said first output flow path for a predetermined first interval, and secondly to direct fluid flow through said second input flow path directly to said dialyzer and from said dialyzer through said second output flow path to said sensor and thence to drain for a second predetermined interval,
   said computer also having means for sampling the electric signals from said sensor during said first and second intervals, storing said electric signals and comparing the flow rates measured during said first and second intervals and producing a display of differential between the higher and lower flow rates, said differential representing the flow rate of ultrafiltrate from said dialyzer.

2. The system according to claim 1 wherein said computer includes adjustable means for setting high and low limits of said ultrafiltrate flow rate and producing high and low limit control signals when said high and low limits are exceeded, and means common to said first and second output flow paths for controlling negative pressure therein in response to said high and low limit control signals.

3. The system according to claim 2 wherein said means common to said first and second output flow paths for controlling negative pressure therein is an air control valve connecting said first and second output flow paths to ambient air.

4. The system according to claim 3 wherein said air control valve is opened when said high ultrafiltrate flow rate is exceeded and is closed when said ultrafiltrate flow rate reaches said low ultrafiltrate flow rate.

5. The system according to claim 3 wherein said first, second and third control valves and said air control valves are solenoid valves.

* * * * *